(12) United States Patent
Schellenberg et al.

(10) Patent No.: US 9,322,930 B2
(45) Date of Patent: Apr. 26, 2016

(54) FLEXIBLE GAMMA CAMERA SYSTEM

(71) Applicant: CUBRESA INC., Winnipeg (CA)

(72) Inventors: James Schellenberg, Winnipeg (CA); Bob Schellenberg, Winnipeg (CA)

(73) Assignee: Cubresa Inc., Winnipeg, MB (CA)

( * ) Notice: Subject to any disclaimer, the term of this patent is extended or adjusted under 35 U.S.C. 154(b) by 19 days.

(21) Appl. No.: 14/378,677

(22) PCT Filed: Feb. 14, 2013

(86) PCT No.: PCT/CA2013/050113
§ 371 (c)(1),
(2) Date: Aug. 14, 2014

(87) PCT Pub. No.: WO2013/120200
PCT Pub. Date: Aug. 22, 2013

(65) Prior Publication Data
US 2015/0001407 A1    Jan. 1, 2015

Related U.S. Application Data

(60) Provisional application No. 61/598,592, filed on Feb. 14, 2012.

(51) Int. Cl.
| | | |
|---|---|---|
| *A61B 6/12* | (2006.01) | |
| *G01T 1/16* | (2006.01) | |
| *G01T 1/164* | (2006.01) | |
| *A61B 6/03* | (2006.01) | |
| *G01T 1/20* | (2006.01) | |
| *G01T 1/208* | (2006.01) | |
| *A61B 6/00* | (2006.01) | |

(52) U.S. Cl.
CPC ............... *G01T 1/1644* (2013.01); *A61B 6/037* (2013.01); *A61B 6/4266* (2013.01); *A61B 6/4405* (2013.01); *A61B 6/502* (2013.01); *A61B 6/547* (2013.01); *G01T 1/1642* (2013.01); *G01T 1/20* (2013.01); *G01T 1/208* (2013.01); *A61B 6/12* (2013.01); *A61B 6/4258* (2013.01); *A61B 6/4417* (2013.01)

(58) Field of Classification Search
CPC ........ A61B 6/037; A61B 6/12; A61B 6/4258; A61B 6/4266; A61B 6/4405; A61B 6/4417; A61B 6/502; A61B 6/547; G01T 1/1642; G01T 1/1644; G01T 1/20; G01T 1/208
See application file for complete search history.

(56) References Cited

U.S. PATENT DOCUMENTS 7,683,331 B2 *   3/2010   Chang .................... A61B 6/037
                                                    250/363.04
2013/0163728 A1 *   6/2013   Silberklang ............ A61B 6/037
                                                    378/177

* cited by examiner

*Primary Examiner* — Mark R Gaworecki
(74) *Attorney, Agent, or Firm* — Michael R. Williams; Ade & Company Inc.

(57) ABSTRACT

Described herein is a gamma camera imaging system in which a plurality of gamma cameras or multiheads are attached at a front face thereof to the outer surface of a flexible substrate. The flexible substrate is capable of forming an inner concave surface which in use is arranged to fit over or around a body part to be analyzed.

5 Claims, 7 Drawing Sheets

Figure 2 A Side View of a Multihead

FLEXIBLE GAMMA CAMERA SYSTEM

PRIOR APPLICATION INFORMATION

This application claims the benefit of US Provisional Patent Application 61/598,592, filed Feb. 14, 2012.

FIELD OF THE INVENTION

The present invention relates to a gamma camera system for radioactive source distribution imaging.

BACKGROUND OF THE INVENTION

Gamma Cameras are used for the detection of gamma rays, typically in the energy range of 40 keV to 511 keV. These cameras can be designed with collimators, scintillators, detectors and electronics, with the detectors being of tube or silicon design, or they may use a more direct detection method that combines the scintillator and detector into a single material, in the manner that is used within CZT cameras. These camera systems are used in medical imaging, pre-clinical imaging, veterinary imaging, and for a variety of other uses including radiation imaging for radioactive material and hazardous material inspection.

Recent advances in silicon photomultiplier detector technology have allowed for a significant reduction in the size of the detector portion of the gamma camera as compared to tube photomultipliers. Examples of silicon photomultipliers are available commercially from companies such as SensL and Hamamatsu. These detectors can be made with pixel sizes from 1 mm to 6 mm, for example, and each pixel has many sub-pixels, of typical size 35 micrometers.

Previously, photomultiplier tubes were used as the detectors in gamma cameras, which caused the camera depth to be many inches. While the scintillator material may be only 5 mm in some cases and the collimator element may only be 20 to 30 mm in some cases, the large size of the tube photomultiplier, and the need for fairly high voltages to be used in tube-based designs, dominated the product design.

Silicon-based detectors of thicknesses measured in mm are now possible, with a depth of 2 to 5 mm or less being possible in some package designs. In addition, the tubes would typically be of a diameter that was an inch or more, whereas the silicon photomultipliers can be made with 1 mm diameters. A recent check of the Hamamatsu website indicated that part R7402 was a compact tube design, and it had a diameter of 16 mm, only 8 mm of which was the "working" or sensing part of the tube. This is in comparison to the SensL products that are currently available, such as the Array 4, which allows a set of 16 photomultipliers of size 3.3 mm×3.3 mm, in a 4 by 4 array, giving a total size of 14 mm×14 mm, including packaging sizes.

Gamma camera systems today can be designed to give two dimensional (planar) or three dimensional images. In order to provide three dimensional imaging, it is necessary to add information from another angle or direction. This approach is called SPECT imaging, and it can be performed either by moving a single gamma camera head between multiple positions or by having more than one gamma camera head located in the multiple positions.

U.S. Pat. No. 5,565,684 entitled Three-dimensional SPECT reconstruction of combined cone-beam and fan-beam data discusses the use of three gamma camera heads mounted onto a gantry for rotation about the patient.

Other SPECT systems are also known.

U.S. Pat. No. 6,242,743 entitled "Non-orbiting tomographic imaging system", discusses the production of tomographic images without moving the detectors or collimators. This is done by "using a plurality of detector modules which are distributed about or around the object of interest and which fully or partially encircle it. The detector modules are positioned close to the object of interest thereby improving spatial resolution and image quality. The plurality of detectors view a portion of the patient or object of interest simultaneously from a plurality of positions. These attributes are achieved by configuring small modular radiation detector with high-resolution collimators in a combination of application-specific acquisition geometries and non-orbital detector module motion sequences composed of tilting, swiveling and translating motions, and combinations of such motions. Various kinds of module geometry and module or collimator motion sequences are possible, and several combinations of such geometry and motion are shown. The geometric configurations may be fixed or variable during the acquisition or between acquisition intervals. Clinical applications of various embodiments of the tomography invention include imaging of the human heart, breast, brain or limbs, or small animals. Methods of using the non-orbiting tomographic imaging system are also included.

U.S. Pat. No. 6,628,984, entitled, "Hand held camera with tomographic capability," describes a tomographic imaging system comprising a moveable detector, a position sensor, and a computational device for integrating the position and angulation of the detector with the emissions that are observed. This allows for a derivation of a three dimensional image.

U.S. Pat. No. 5,939,724, to Eisen, et al., issued on Aug. 17, 1999, and entitled, "Light weight-camera head and -camera assemblies containing it," describes a light weight gamma-camera head and assemblies and kits which embody it. The gamma-camera head has a detector assembly which includes an array of room temperature, solid state spectroscopy grade detectors each associated with a collimator and preamplifier, which detectors and associated collimators and preamplifiers are arranged in parallel rows extending in a first direction and suitably spaced from each other in a second direction normal to the first direction, each of the parallel detector rows holding a plurality of detectors. The head may optionally have an electric motor for moving the detector in the second direction and optionally also in the first direction, either stepwise or continuously.

U.S. Pat. No. 6,525,320, to Juni, issued on Feb. 25, 2003, and entitled, Single photon emission computed tomography system, describes a single photon emission computed tomography system, which produces multiple tomographic images of the type representing a three-dimensional distribution of a photon-emitting radioisotope. The system has a base including a patient support for supporting a patient such that a portion of the patient is located in a field of view. A longitudinal axis is defined through the field of view. A detector module is adjacent the field of view and includes a photon-responsive detector. The detector is an elongated strip with a central axis that is generally parallel to the longitudinal axis. The detector is operable to detect if a photon strikes the detector. The detector can also determine a position along the length of the strip where a photon is detected. A photon-blocking member is positioned between the field of view and the detector. The blocking member has an aperture slot for passage of photons aligned with the aperture slot. The slot is generally parallel to the longitudinal axis. A line of response is defined from the detector through the aperture. A displacement device moves either the detector module or the photon-blocking member relative to the other so that the aperture is displaced relative to the detector and the line of response is swept across at least a portion of the field of view.

U.S. Pat. No. 6,271,525, to Majewski, et al., issued on Aug. 7, 2001, and entitled, "Mini gamma camera, camera system and method of use," describes a gamma camera, which comprises essentially and in order from the front outer or gamma ray impinging surface: 1) a collimator, 2) a scintillator layer, 3) a light guide, 4) an array of position sensitive, high resolution photomultiplier tubes, and 5) printed circuitry for receipt of the output of the photomultipliers. There is also described, a system wherein the output supplied by the high resolution, position sensitive photomultiplier tubes is communicated to: a) a digitizer and b) a computer where it is processed using advanced image processing techniques and a specific algorithm to calculate the center of gravity of any abnormality observed during imaging, and c) optional image display and telecommunications ports.

U.S. Pat. No. 6,212,423, to Krakovitz, issued on Apr. 3, 2001 and entitled, "Diagnostic hybrid probes," describes a hybrid nuclear and ultrasonic probe, comprising a cylindrical outer casing surrounding a nuclear probe, which comprises two scintillator plates intersecting perpendicularly, each of the scintillator plates having a plurality of parallel collimators; and an ultrasonic probe situated between said casing at the intersection of said scintillator plates.

U.S. Pat. No. 7,705,316 entitled Dynamic SPECT camera discusses a SPECT camera that has a plurality of single-pixel detectors, which can be moved, and which includes a position-tracker that provides information on where the detectors are at each point in time, and which includes a time-binning method. In this way, radioactive emissions can be collected from different positions at different times, and then software can be used to create the 3D image at a later time.

U.S. Pat. No. 8,338,788 entitled Method and system of optimized volumetric imaging describes a system that performs a volumetric scan. The system uses a plurality of extendable detector arms with each detector arm having a detection unit, supported by an actuator and gantry. The types of methods that have been discussed in U.S. Pat. No. 8,338,788 and U.S. Pat. No. 7,705,316 attempt to control the position of the gamma camera heads using attachments on the back of the detector heads.

In the case where a single gamma camera head is moved, it will be moved between two or more positions in some known fashion, such as on a mechanical track, rail or arm. This approach will take a certain number of minutes at one location and then will move to the second location, where it will take another block of a certain number of minutes.

In the case where multiple gamma camera heads are available, the heads may be held in two or more positions for a certain number of minutes, as discussed in U.S. Pat. No. 7,705,316 or U.S. Pat. No. 8,338,788. Arms and gantries have typically been used to move the camera heads.

The first approach may be better for equipment cost, as long as the gamma camera head moving apparatus is less costly than the second head. The second approach is better if one wants to get an image in as short a time as possible, or if one is observing simultaneous radionuclide movements. Typical positioning methods allow two gamma camera heads to be between 40 and 90 degrees apart in order to have sufficient information to achieve good spatial resolution in all three directions. Another approach to SPECT imaging is to allow handheld operation of the gamma camera, and then to have positioning system and software automatically align the positioning information with the gamma camera counts information, thereby allowing a 3D image of the radiating object to be obtained. This method is used by SurgicEye in their designs, discussed in US patent application 20090259123.

The idea of using a flexible substrate to mount gamma detectors has been discussed in Published US Patent Application 20090321650. In this case, they are using a specific design of detectors that may be individually stimulated by a detector reader. Their intended application relates to radiation monitoring and security.

Interest in flexible scintillators has been shown in previous patents, including U.S. Pat. No. 6,563,120 entitled Flexible radiation detector scintillator, in which a plastic scintillator was cut in elongated slices, and these slices slid relative to one another to allow 2-d flexibility to be achieved.

Another approach to a flexible scintillator has been taken in U.S. Pat. No. 7,132,662 entitled Flexible liquid-filled radiation detector scintillator, which uses a tube filled with liquid scintillating material. These inventors also considered the thermal expansion concerns of the liquid.

SUMMARY OF THE INVENTION

According to a first aspect of the invention, there is provided a gamma camera imaging system comprising:
  a plurality of gamma camera heads, each respective one of said plurality of gamma camera heads comprising a collimator, a scintillator, a detector and a read-out system, each said respective one of said plurality of gamma camera heads being individually mounted to a flexible substrate;
  a flexible substrate capable of forming a concave inner surface and having an outer surface;
  an interface module; and
  an operating system,
  wherein each respective one of said plurality of gamma camera heads is mounted to the outer surface of the flexible substrate at a front face thereof.

According to a further aspect of the invention, there is provided a gamma camera system comprising:
  a flexible substrate capable of forming a concave inner surface and having an outer surface;
  a plurality of gamma camera heads, each respective one of said gamma camera heads comprising a collimator, scintillator, detector and read-out electronics system;
  a position identification system for determining the position of said each respective one of the plurality of gamma camera heads;
  a movement system for moving the flexible substrate and the respective ones of the plurality of gamma camera heads to be moved so as to optimize imaging parameters; and
  an operating system that controls movement and identification of positioning, and which provides gamma camera imaging software for planar or SPECT imaging,
  wherein each respective one of said plurality of gamma camera heads is mounted to the outer surface of the flexible substrate at a front face thereof.

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

For advanced SPECT imaging using silicon photomultipliers, there is an interest in using small gamma camera systems that can easily be positioned in areas such as the underarm, the jaw area, around the breast, leg or arm, or inside the body for surgical imaging.

For this reason, there exists a need to have a simple manner to control the positions of very small gamma camera heads. One method would be to use articulated arms that hold the gamma cameras, however as the number of gamma camera heads increases to 100 and above in a confined space, the logistics of 100 articulated arms in a small space begin to be excessive. In addition, for a more flexible gamma camera system, the curvature of the SPECT camera would vary depending on the size of the breast, arm, leg, underarm or jawbone. In addition, the curvature of the SPECT system might also vary depending on the size and location of the lesion in question. In addition, the curvature and positioning of the SPECT camera might change depending on the number of lesions in the breast, leg, arm or other body part, and on the size and spatial distribution of these more than one lesions. For all of these reasons, a more advanced way of positioning small gamma camera heads for improved imaging is desired.

For the breast imaging application case in which the breast is immobilized and MRI imaging has already occurred, the location of the suspicious lesion or lesions is already known. MRI is highly sensitive, with sensitivities approaching 100%, and so additional lesions will not be uncovered by the gamma imaging system. Instead, it may be possible to use the gamma imaging system to add additional and improved and differentiated information about a suspicious lesion so that better interventional and intra-operative decision making can be done.

As an example of a method to optimize lesion imaging, if the breast lesion is of size 5 mm, and if it is located approximately 3 cm below the breast surface, one could use a small compact gamma camera of size 50 mm×50 mm to image the volume around the lesion. In this case, if a parallel hole collimator is used, the central portion of the gamma camera will be imaging the lesion volume and the external portion of the gamma camera will be imaging breast tissue where no lesion is found. That is, only 5×5 mm of the total 50×50 mm imaging surface is pointed at the lesion. It is necessary to image a portion of the surrounding tissue around the lesion in order to obtain a background count level and in order to obtain an accurate idea of the tumor extent and boundary, however an approximate estimate for the amount of boundary region needed to be imaged would be about the size of the lesion, which is 5 mm on either side. Therefore, approximately 15 mm of the 50 mm gamma camera is pointed in a right orientation, and the remaining 35 mm is not pointed at a lesion and its surrounding tissue.

Of course, if the lesion is of large size, say 15 mm, then the entire 50 mm×50 mm gamma camera face may be pointed in a useful way to image that lesion and its surrounding tissues. Of course, if a larger gamma camera was used, say 150×150 mm face size, then the majority of the gamma camera would not be useful in the imaging of the single lesion of size 5 mm which is 3 cm below the surface of the skin.

One of the fundamental problems is therefore that there may be one or more lesions requiring imaging, and they will be of varying sizes and in various locations in the breast. In addition, the breast size for different women will vary from patient to patient. One design approach for the general case is to place multiple gamma cameras to view multiple lesions, however it would be best if these multiple gamma cameras could all view the same lesion in the case where only one lesion needs to be studied, or could view multiple lesions in the case where multiple lesions need to be studied. This would imply that the cameras would need to be moveable. To do this, one could place multiple cameras on multiple articulated arms. For small lesions of say 3 mm in size, one might want multiple gamma cameras of size 6 mm×6 mm, arranged in an arc or half-sphere around the lesion being studied. As the size of the lesion decreases and as the distance from the skin surface to the lesion decreases, the size of the gamma camera required can also decrease, thereby saving cost. Cabling and wiring, however, may become more complex as the number of gamma cameras increase.

For all these reasons, a more elegant and useful approach to having a flexible positioning system for multiple gamma cameras is to attach the front collimator surface or front package surface directly in front of the collimator for each gamma camera head to a flexible surface that can be flexed to image different lesion geometries, and potentially different sizes of breasts, and potentially different body parts.

A flexibly-mounted multi-headed gamma camera for use in imaging radioactive source distributions is herein described. A large number of small gamma camera heads, with each head consisting of at least collimator, scintillator, detector and read-out electronics or read-out system, are attached to a flexible substrate, and position control and position detection systems are also attached to the substrate and camera systems. The detector is for example a silicon photomultiplier, the scintillator is for example CsI(Tl), and the collimator is for example made of lead or tungsten with parallel hole collimation.

In preferred embodiments, the flexible gamma camera has wiring to allow powering, signal readout, clocking and various other functions to occur.

As discussed herein, the flexible gamma camera system can be overlaid on a volume or area of interest, such as, in human imaging, the breast, neck, arm, leg, or other portion of the body that is contoured, and this flexible gamma camera will allow a SPECT imaging session to be performed.

The flexible gamma camera system may be located inside a housing which is held away from the source distribution.

In preferred embodiments, as discussed below, the exact positioning of the gamma camera heads is controlled by a position control system, which allows the flexible gamma camera to optimize its imaging for specific functions and needs. The exact position of the gamma camera heads may be determined using any of a variety of means known in the art, including but by no means limited to optical and electromagnetic fiducial methods that are known in the art, as used by Northern Digital, Ascension Technologies, Roper Ind., or other known position measurement systems.

According to an aspect of the invention, there is provided a gamma camera imaging system comprising:
  a multihead, which is a plurality of gamma camera heads, each respective one of said plurality of gamma camera heads comprising a collimator, a scintillator, a detector and a read-out system, each said respective one of said plurality of gamma camera heads being individually mounted to a flexible substrate;
  an interface module which provides analog to digital signal conversion, buffering of digital contents, conversion of physical media from copper to fiber for those applications that require fiber output in order to go through an MRI room waveguide, generation of a system clock that can be used to synchronize the gamma camera head to the interface module, generation of a controllable reset line that will reset the gamma camera head and interface module to ensure that pixel 1 digital voltage values are placed in buffer 1 position); and
  an operating system which is typically a computer with monitor, processing capability and keyboard and mouse, and provides event processing, sub-pixel resolution, user interface, image processing and anti-noise processing algorithms, and which provides position control algorithms and processing for the position control system, and which provides position measurement processing capability for the position measurement system.

In a preferred embodiment, the flexible substrate is arranged to form a concave inner surface for being fitted around a body portion such as a breast, neck, arm, leg, or other portion of the body that is contoured, for imaging said body portion. The plurality of gamma cameras or multiheads are mounted onto the flexible substrate such that a front face of the gamma camera is mounted to an outer surface of the flexible substrate, as shown in the accompanying drawings. As will be appreciated by one of skill in the art, as a result of this arrangement, the flexible substrate can be formed into the concave shape and fitted around a body part to be imaged such that each of the respective ones of the plurality of gamma cameras are pointing at the body portion to be imaged.

As will be appreciated by one of skill in the art, this is in contrast with prior art methods in which the gamma cameras are held from behind by a robotic arm.

In a preferred embodiment, the gamma camera imaging system further includes a movement system for moving said plurality of gamma cameras, as discussed below.

In a preferred embodiment, the gamma camera imaging system further includes a position identification system such that the location of each respective one of the plurality of gamma camera heads can be determined, as discussed herein.

In preferred embodiments, the gamma camera system comprises a flexible surface with a plurality of gamma camera heads, with each head comprising a collimator, scintillator, detector and read-out electronics system, with the multiple heads positioned on the flexible substrate and affixed to the surface thereof, a position identification system that allows the position of all or substantially all of the camera heads to be identified, a movement system that allows the flexible substrate and the camera heads to be moved so as to optimize imaging, optimize noise rejection, or other imaging parameters that need optimization, and an operating system that allows for control of movement, identification of positioning, and which provides gamma camera imaging software for planar and/or SPECT imaging, as required by the user of the equipment.

As will be appreciated by one of skill in the art, the gamma camera imaging system described herein is useful in those cases where the size of the multihead needs to be kept as small as possible. For example, for situations in which the gamma camera will be made MR-compliant and will be inserted close to the pendant breasts of a patient who is receiving breast MRI imaging, it is important that a small camera is used to allow many imaging geometries to be used. For example, in some cases a breast biopsy should be performed from the lateral direction, because the potentially cancerous lesion inside the breast is closest to the lateral, or outside, of the breast. In other cases, the breast lesion is closest to the medial, or sternum, location, and should be approved from the medial direction. In other cases, the approach will be from another direction or angle. For medial access situations, if medial imaging is required, the only way that imaging with both breasts pendant can be done is if the gamma camera height is very small, so that the small cleavage space between the breasts can be used for the imaging. In some cases, one breast may be pendant while the other breast is held up out of the way, however this is not true in all cases, not is it desired that only one breast should be imaged at a time. Alternatively, if both breasts are pendant but medial imaging is desired for one breast, then the gamma camera will need to fit within the cleavage gap and as close to the sternum as possible to allow more complete imaging. The cleavage gap will only be a few cm in size in this case, and so a gamma camera with as small a height as possible is desired. In the case where additional underarm imaging might be desired to check for lymph nodes, a small multihead can be fit most easily within the various positions that an underarm location may be required. In addition, for those cases in which the practitioner can place the gamma camera directly against the breast, and may push the gamma camera into the breast in order to produce as much recorded activity as possible from a suspicious lesion, it is easiest to push into the breast with a smaller camera rather than a larger camera.

This design architecture is also useful because it moves the processing of the events to be implemented in software, which allows easy software upgrade to the image and signal processing algorithms.

Figure 1A:
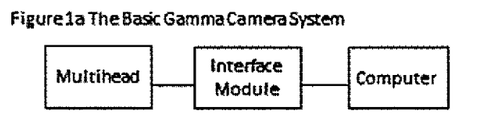
FIG. 1 shows the architecture of the basic gamma camera system.

The system is shown in simplest form in FIG. 1a, in which a single multihead gamma camera is connected to an interface module which is connected to a computer.

Figure 1B:
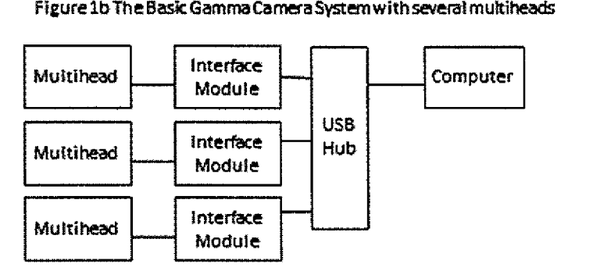

FIG. 1b shows an embodiment where more than one multihead is desired, and in this case there are three multiheads, three interface modules (IFM), and a USB hub is added to allow networking back to the computer. If the bandwidth requirement of the system is high, Gig E or some other higher speed point to point networking method can be used to connect to the computer. If the processing requirements are high, a higher speed computer may be used to allow the algorithms to perform at the required speed.

Figure 2:
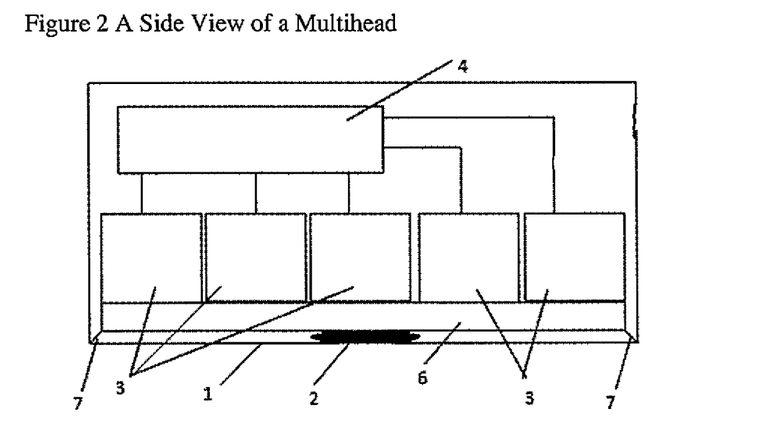
FIG. 2 shows the multihead architecture diagram.

FIG. 2 shows a side view of a multihead. There are five gamma camera heads 3 which connect back to the electronics box 4. The electronics box 4 aggregates the connections for optimum packaging and routing. The electronics box 4 connects to the IFM. The electronics box may also provide the air pressure control, and may provide other control functions such as temperature monitoring, self-test and gamma camera head position measurement. In this configuration, the air balloon 2 can be inflated and deflated, which moves the flexible substrate 6 up and down, providing more or less curvature. The clearance to the edges of the package determines the maximum amount of curvature that can be used in this design. The edge control wires 7 are springs and pull the edge back tight so that the flexible substrate is returned to a flat configuration from a concave configuration when the air is sucked out of the balloon. These pieces are all held within an exterior package 1. With the use of these edge control wires 7, the air balloon 2 does not need to be glued or attached to the flexible substrate, which allows the air balloon 2 change-out or replacement to be done as easily as possible.

As will become apparent to one of skill in the art, the purpose of this flexibility approach to gamma camera positioning is to allow optimum SPECT imaging to occur in various lesion sizes, orientations, and in various depths and distances from the gamma camera.

Figure 3:
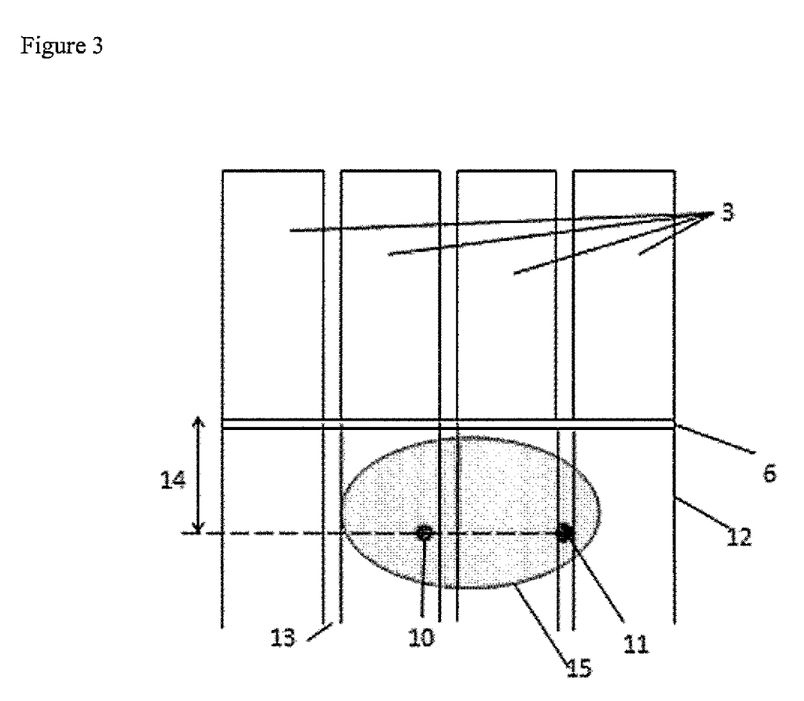
FIG. 3 shows a multihead simplified diagram in flat position with two lesions.

FIG. 3 shows a simplified view of a gamma camera imaging a breast with two lesions. This is side view of a multihead with four gamma camera heads 3 pointing directly down towards a breast volume 15 in which a first lesion 10 and a second lesion 11 are shown. The flexible substrate 6 supports the gamma camera heads 3. Also shown are the viewing angles 12 as a guide to the eye. These viewing angles are not physical elements, but instead show that the gamma camera heads 3 will view radioactive objects that are in front of them. In this case, it is assumed that the gamma camera head 3 is using a lead parallel hole collimator with parameters of 23 mm depth, 1.5 mm hexagonal holes and 0.2 mm septal thickness. With this type of collimator, the viewing angle in front of the gamma camera head 3 diverges at a rate of 4 degrees from the front of the collimator, and therefore the viewing angles 12 are at a 4 degree expanding angle to the perpendicular. The gap between the gamma camera heads 13 will depend on the design of the multihead, and can be for example 4 mm in size. If the distance from the lesion to the front of the collimator 14 is a typical distance for breast imaging of for example 23 mm, these geometrical distances imply that if the second lesion 11 is 1 mm or smaller, than there will be no portion of the second lesion 11 that can be observed by the gamma camera in its current position. If the second lesion 11 is larger, then a small portion of the radioactivity of the lesion will be visible by the gamma camera, as can be seen in FIG. 3.

FIG. 3 shows a non-flexible gamma camera pointed at a first lesion 10 and a second lesion 11. The lesion 10 is imaged only by the second of the four camera heads 3, but not by the other heads 3. Even though these other heads could be useful in improving the image, there is no method to position them for this particular case, and so their imaging angles lie outside the breast volume 15. Even in the case of MR-SPECT hybrid imaging, in which case the operator knows which lesion is of interest and knows the location thereof, it is not possible to bend the camera to allow better imaging to occur because as discussed above the second lesion 11 is currently position in the gap between the gamma camera heads 3. For small lesions and for systems with large gaps between the detection heads, it is possible that the detection of "second" lesion 11 situations will not be as good as for lesions that fall within a "first" lesion 10 type of location. A typical collimator used for this type of imaging can be, for example, a Nuclear Fields hexagonal hole collimator with 1.5 mm hole sizes, a 0.2 mm septal thickness and a depth of 23 mm. Such a collimator is very directional as already indicated.

Figure 4:
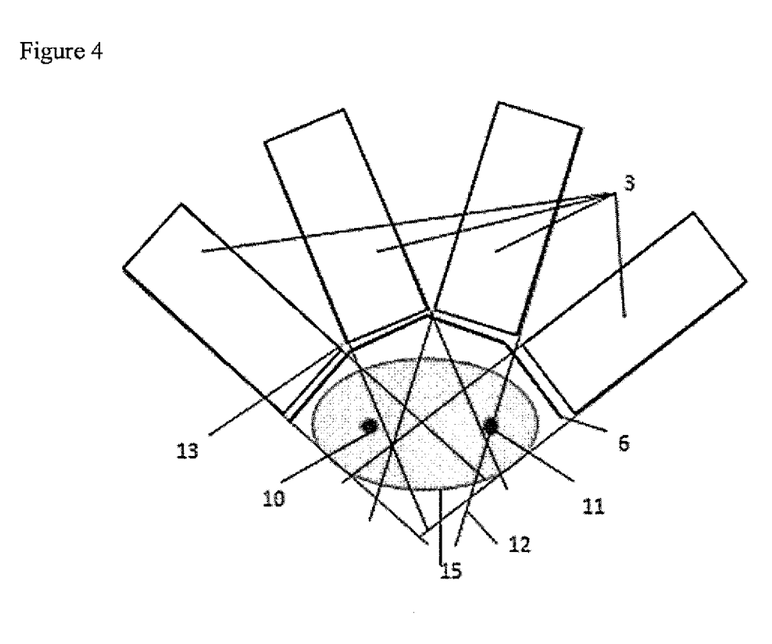
FIG. 4 shows the multihead simplified diagram in flex position with two lesions.

In contrast, FIG. 4 shows a flexible multihead being used to image the breast volume 15. This level of flexibility in positioning is obtained by using a flexible substrate 6, onto which the multiple gamma camera heads 3 are attached. With this flexing of the multihead, the entire breast is more optimally imaged, and the two lesions are both imaged by one or more of the gamma camera heads. SPECT image processing can now be used on some of the volume of the breast. The gap between the gamma camera heads 13 remains the same distance, because the gamma camera heads are firmly affixed to the flexible substrate. The flexible substrate does not flex throughout its distance, because the front of the gamma camera heads use a rigid lead collimator, and so the flexible substrate can only bend at the locations between the gamma camera heads.

The gain that flexing can provide is related to the change in the total solid angle that is provided by the gamma camera. In a standard parallel hole collimator system, the sensitivity of the camera does not change with distance because the collimator cannot be flexed. For a four-headed multihead as shown in FIGS. 3 and 4, if we assume that a lesion is 40 mm from the front of the flexible substrate surface, and that the flexing can be done optimally, and that the camera heads are 20 mm one a side and are packed tightly together, we have an improvement in the solid angle of 2.95 times, as shown below. This improvement can be used to improve the sensitivity, reduce the dosage, or reduce the imaging time. Table 1 below is for a "first" lesion 10 case in which in the unflexed position, the camera heads 3a, 3c and 3d do not receive any radiation from the lesion as shown in FIG. 3, but when they are optimally flexed all four cameras receive radiation from the first lesion as shown in FIG. 4.

Solid Angle Change—4 Headed Camera

|  | 1 | 2 | 3 | 4 | Total |
|---|---|---|---|---|---|
| not flexed | 0 | 0 | 0.019904 | 0 | 0.019904 |
| flexed | 0.010155 | 0.01645 | 0.015727 | 0.01645 | 0.058782 | camera 3 is back off 5 mm
Gain in Solid Angle from Flexing 2.95322

Table 1 provides numbers for the gain in solid angle that occurs through flexing the gamma camera.

In this case, when the flexing occurs, camera head 3c retreats from the front surface, and so the distance from the lesion 1 to the camera head collimator front surface increases from 40 mm to 45 mm. Camera head 3b and 3d, however, can observe the first lesion 10 at a distance of 44 m, and camera head 3a will observe the radiation at a slightly greater distance of approximately 56 mm. These are approximate distances, and are measured to the middle of the collimator face.

Figure 5:
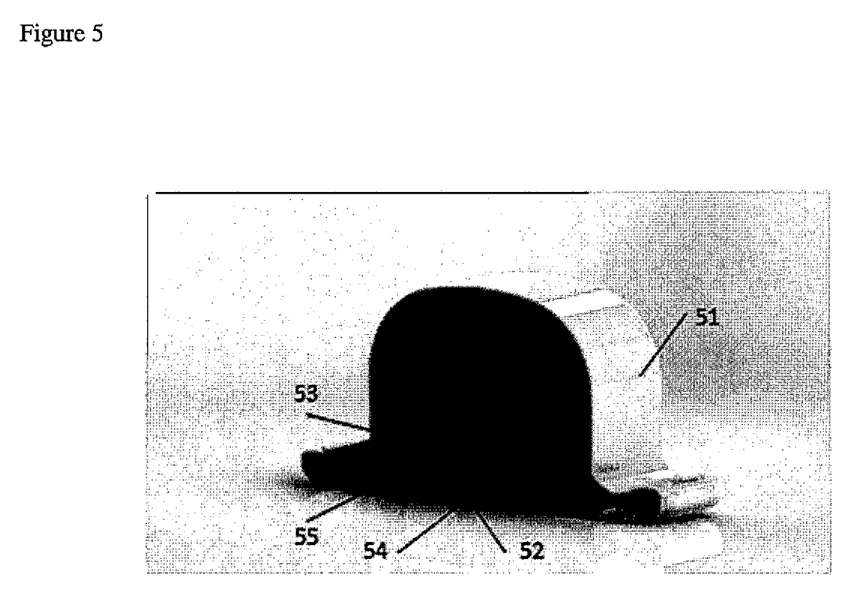
FIG. 5 shows a multihead detail in flat position including packaging.

FIG. 5 is a rendering of a multihead that allows curvature in 2 dimensions to occur. The exterior package 51 is used to hold multiple gamma camera heads 53. The air balloon 52 is located against the bottom of the package. The bottom of the package 54 does not curve, but is instead maintained flat and is sufficiently rigid to provide mechanical stability as the air balloon provides curvature to the gamma camera multihead system. Extending off of the back of each camera head is the readout board 55 appropriate for that camera head. The readout boards are connected to the electronics system, which then connects to the interface module IFM. In this embodiment, the air balloon is connected via an air tube to a simple pump ball mechanism, which allows the user to adjust the bend of the gamma camera. The readout wires, fiducial wires, air tubing, and electronics box are not shown in this rendering.

Figure 6:
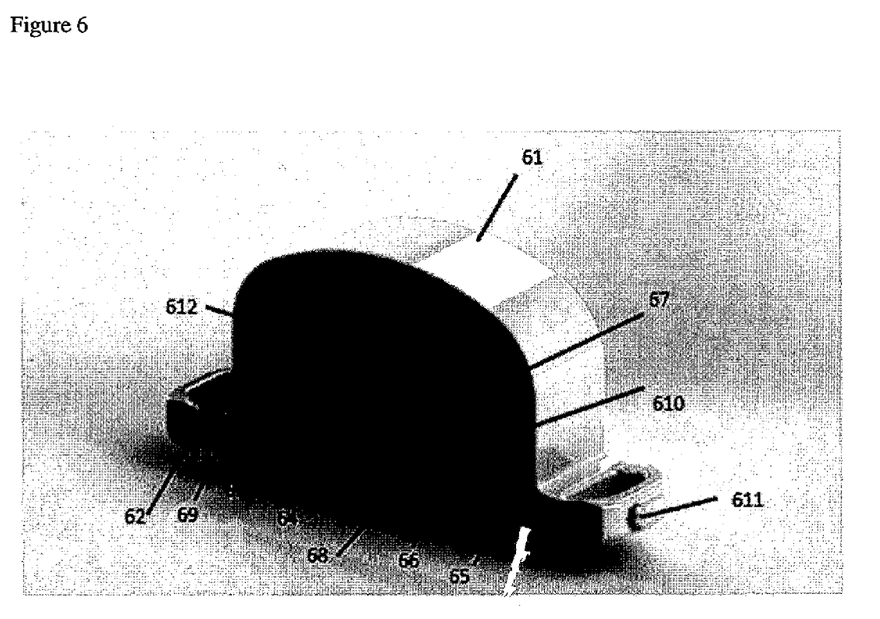
FIG. 6 shows a multihead detail in flex position with an air balloon as the flexing method and packaging.

FIG. 6 shows the same multihead in additional detail with the flex operation occurring. In this case, the inflatable air balloon 64 is inflated using air pump 611 via air tubes 65, with the air pump located on the handle 62. Each row of gamma camera heads 610 is located within a lead shield box 66. The shield box may alternatively be made from tungsten. The row ends of the gamma camera heads roll on rollers 68 to allow easy movement of the ends, because the ends are pulled into towards the middle of the gamma camera as the flex occurs. The gamma camera heads comprise collimator, scintillator and detector 610 and readout boards 67. The shape and size of the exterior case 61 determines the allowable amount of flex, because the readout boards 67 cannot hit the side of the case. The amount of flex is determined by the stops that are designed within the enclosure. These stops are not shown. The amount of flex that occurs can be determined using electromagnetic fiducials and fiducial wiring 69. The EM fiducials operate within the measurement volume dictated by the magnet system, not shown, as is normal for Ascension Technologies and other electromagnetic position measurement systems. The amount of flex determines the amount of overlap that exists between the collimator holes, which therefore determines the amount of imaging improvement that will occur in this design. The electronics box 613 aggregates and coordinates the read out board wires 612, the fiducial wires 69, and provides command and control and interconnection functionality back to the IFM box. The IFM box and the connection wiring to the multihead are not shown. The air pressure release valve is also not shown.

As will be apparent to one of skill in the art, there are several algorithmic approaches that can be used in determining how much flex to provide to the surface and are well within the knowledge of one of skill in the art. For example, one simple approach is to monitor the sensitivity of the gamma camera with the surface flat, and then to flex a little bit, and watch the sensitivity to see if it improves. This approach can be incorporated into an automatic control system, and so the user can turn on the flex button and the system will self-flex.

For lesions that are smaller than the total size of the gamma camera, flexing will always lead to an improved sensitivity. For example, if the multihead has 4 gamma camera heads of 20 mm square each, making the entire multihead a linear distance of 80 mm, then any lesion smaller than 80 mm can benefit from having some flex in the system. In the case where the lesion is 70 mm in size, you would expect only a little flexing to provide the largest sensitivity, whereas in the case where the lesion is quite small, say 10 mm in size, the system can flex a lot before the highest sensitivity is achieved. As will be appreciated by one of skill in the art, any suitable algorithm will have stops built into the software so that the system is not over-flexed. There will also be mechanical stops built into the system to ensure that the flex does not go too far, causing the PCB boards to hit the outside of the case, or causing the flexible material to be over-flexed, as discussed above.

For any position of the multihead, the magnetic position measurement system can automatically measure the position of all of the elements, using methods known in the art, for example, as available from Ascension Technologies or other similar companies.

Figure 7:
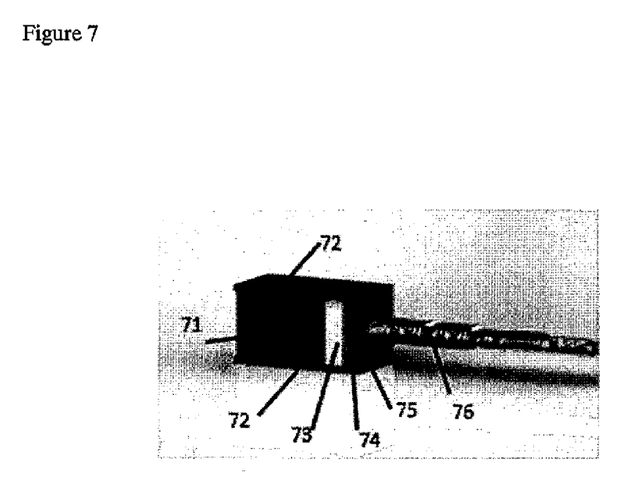
FIG. 7 shows a detail of a single gamma camera head showing collimator, scintillator, detector and readout board.

FIG. 7 shows a typical camera head, which shows one version of the CSDE (Collimator, Scintillator, Detector, read out Electronics) arrangement. The collimator 71 is 23 mm deep, the scintillator 73 has a thickness of 5 mm, the detector 74 is about 2 mm in depth with pins off the back, a small PCB 75 A11 readout board is used in the back of the detector to organize the connections, and the larger PCB 76 A12 readout board is inserted into the connection organization PCB to allow the read-out electronics to be used. A common scintillator that can be used in this case is CsI(Tl) pixelated on approximately 3.5 mm pixellations, in order to match up with the pixel size of the Array 4 detector from Sensl. On the four sides are located lead shielding 72 of thickness 1.5 mm.

Figure 8:
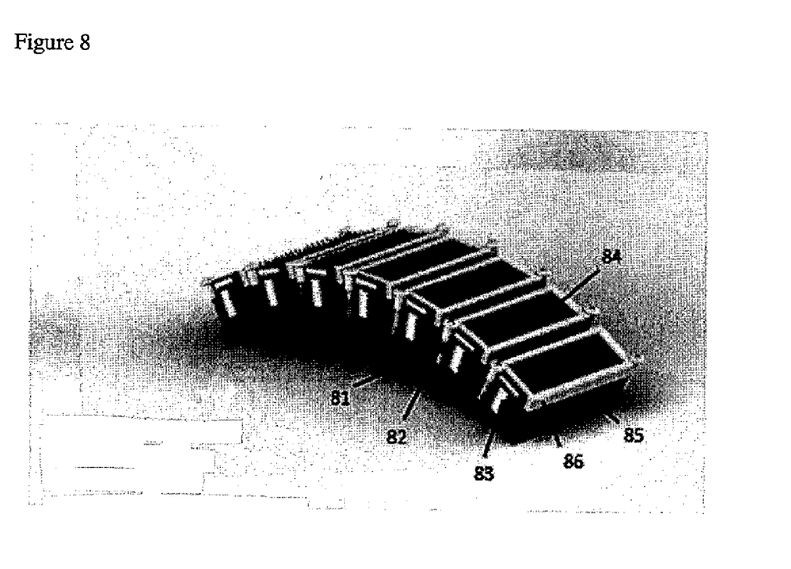
FIG. 8 shows an example of a more advanced design in which the readout PCB is moved to the end of the row and the height of the multihead is reduced. In this case, there is no external package over top of the multihead and so shielding is required around the sides of the rows and forms part of the hold-down bracket.

Further advances can be made with packaging as one reduces the size of the PCB read out boards via integration. FIG. 8 shows a flexible array in which the PCBs have been shrunk in size and repositioned along the side of the row. There is again 6 rows of 3 Array 4's each, however over the top of the row is a common connection plate 84 that connects all of the pins on the back of the Array 4 into the read out PCB 83 that is on the side of the row. As well, in this case a different collimator depth of 10 mm is used, instead of the 23 mm previously used in the other Figures. As the collimator depth decreases, the noise level that penetrates the collimator increases, and so noise reduction and anti-noise software needs to be employed to ensure good performance. The multihead in FIG. 8 is based on the Sensl Array 4 which is nominally 15×15 mm square and 2 mm high. The Array 4 is available in various package styles, including pins grid array and ball grid array which allows a lower profile. The common connection plate 84 over the top of 3 detectors provides additional mechanical stability as well as electrical connection, and the common connection plate connects to the readout PCB on the side of the row. This design also uses lead shielding boxes 81, screw supports 82 that allow the rows to be assembled, and a hold down bracket 86 through which the screw support is used. The collimator, scintillator and detector 85 are just visible through the gap between the lead shielding box and the hold-down bracket. This arrangement and assembly can be flexed by hand by the operator, and will typically have an external package over top that allows the flexibility to occur. The wiring is not shown. The electromagnetic fiducials in this case are also not shown. This multihead will typically be used, for example, with a neck surgical patient in which the magnet for em position measurement is located below the supine patient's neck area, the patient then lies down on the table, and then the flexible multihead is placed on the patient's neck area to be imaged the multihead is connected to the interface module IFM.

The system described includes three main interacting subsystems: the gamma imaging system, the position detection system, and the position control system. The gamma imaging system consists of multiple gamma camera heads that are held in some position, the IFM digital processing system, and the computer processing system. The position detection system consists of fiducials attached to the gamma camera heads, a magnet located below or above or in the vicinity of the item being imaged, and the hardware and software required for the EM measurement system in the way that is standard in the art, as is provided commercially by Ascension Technologies. The position control system in this a simple case is an air bag that can be filled using a ball pump, and which can allow the air to be released using a release valve. The position control system may or may not include software algorithms to automatically provide movement of the camera, or to provide suggestions and feedback to the operator, or the position control system can simply allow the user to pump the air balloon herself.

The image processing system uses position information from the position detection system to allow it to do SPECT processing or other processing, but does not need any information from the position control system. If additional curvature is required, additional air can be pumped into the air balloon. The image processing system may provide guidance to the operator in order to indicate whether more or less curvature, and air, is required within the bladder. Alternatively, the only guidance provided may be the sensitivity measurement as discussed above.

The position control system may have a priori knowledge of the location of lesions from CT or MRI anatomical imaging sessions, or there may be no a priori information.

The lesion being imaged may be selected from the group consisting of a breast lesion, a sentinel lymph node, a lymph node in the lymphatic system, or some other lesion of interest. Any lesion or body part of interest that can benefit from a system that maximizes the sensitivity of the captured radiation emissions is suitable for this type of system, including heart imaging.

One aspect of this invention is that the amount of flex curvature required is different for different situations and for different patients, and so the gamma camera system described can be used to suit a wide variety of patient needs.

Another reason for providing the flexibility for this system is that altering the viewing angle for the volume in question can sometimes lead to changes in the noise levels that are received, which can also allow an improvement in imaging to occur.

Another reason for providing this flexing is in the case of the "second" lesion 11 as discussed above, in which a lesion is located at a midpoint in the gap between imaging elements. In this case, the flexing of the surface allows different viewing angles to be used for the same volume, leading to improved and more complete imaging of the volume in question. As discussed above, when the surface is flexed, the positions of the camera heads can be measured using an electromagnetic method that allows complete knowledge of the camera head position to be achieved, and which therefore allows SPECT image processing to occur in which multiple cameras view the same volume, leading to 3d SPECT images.

It is also important to note that the input of air to the air balloon can be placed under computer control, and the position control system may therefore use automated algorithms and methods to provide optimized imaging.

The multihead will typically require shielding of the scintillators and detector areas, and this can be accomplished either by encasing all of the multihead in an enclosure, and the enclosure has shielding, or each individual camera head can have lead shielding. This approach can be used in the case where one wants the maximum flexibility of positioning.

Figure 9:
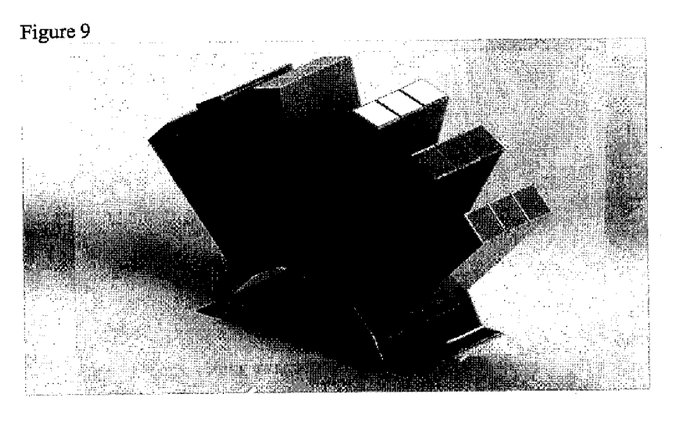
FIG. 9 shows a multihead simplified diagram which does not have a mechanical or automated movement system, but instead can be positioned by hand.

FIG. 9 shows a multihead without the PCBs showing, but instead has an enclosure around each camera head. In this case, each small enclosure has lead shielding, and this system requires more space between the camera heads than a system in which has already been described. Typically, there will be 1.5 mm of lead shielding on all four sides, and so if the package thickness is 1 mm and the lead is 1.5, this leads to a total distance between the camera heads of 5 mm, which might allow for "second" lesion type situations to arise. In FIG. 8 no automatic movement system is shown. Instead, it is assumed that movement comes from the operator picking the multihead up and placing it on the item of interest. For example, there can be a thyroid patient that is lying down on a table, with the magnetic position measurement magnet below the table, and the multihead can be laid over the throat of the patient like a blanket. In this case, each camera head can have its position measured, and the SPECT image of the throat area can be achieved. The FIG. 8 does not show the EM fiducials for the position measurement system, and does not show any wiring. Also note that the height of the camera heads is determined by the PCB height, and that as integration of electronics occurs the height can be reduced to 5 mm or below. Such a small height will allow the system to be used more like a blanket instead of a taller structure.

For each of these designs, the lead shield box of the collimator is typically glued or attached onto the flexible surface. This approach to a flexible gamma camera with closely spaced gamma camera heads is only possible for concave movements, because if the surface goes convex then the readout boards will hit each other. If convexity is desired, the gamma camera heads can be spaced further apart to allow this movement to occur. The amount of convexity will be related to the spacing between the camera heads and the height of the readout portion of the camera heads. The height of the camera heads can be modified by moving the PCB to the side as presented in this discussion.

The positioning measurement system has been discussed in magnetic terms as is common with Ascension Technology methods, and this means that a magnet must be somewhere close to the multihead so that the position of the heads can be measured. In the case of the hand positioned camera blanket, if optical fiducials are used on the camera heads then optical position measurement is possible, in any of a variety of manners known in the art, for example, as long as there is the appropriate infrared camera system as is available from Northern Digital.

The gamma camera elements are made up of a collimator, scintillator, detector and suitable electronics for analog and digital signal processing, powering, status and mode control and other functions. Using technology available in simple design methods today, in some embodiments, the gamma camera will be 80 mm to 120 mm in height and approximately, for example, 14×14 mm in length and width. These are the typical dimensions of the Cubresa GCH1501 design. In these embodiments, the height of the gamma camera would consist of 20 mm for the collimator (a lead collimator available from Nuclear Fields, for example), 5 mm for the scintillator (a CsI(Tl) scintillator that allows approximately 80% stopping power at 140 keV energies, for example), 10 mm for the detector (which might be a SensL Array 4), and the remaining depth used for the electronics boards, cabling and connectorization, and packaging space. This is a high, narrow camera element. By placing many elements on a flexible surface, all next to one another, it is possible to make a flexible camera surface. The camera elements can be flexed easily in various directions so that different lesion sizes and shapes can be optimally imaged.

Having many camera elements on the flexible surface may make it necessary to have an interconnection system on the rear of the elements that provides mechanical support. The common connection plate is one example of a method. This is used so that undue moment of force does not cause damage to the system or cause the elements to fall over. The collimator will be the majority of the weight, and therefore the majority of the weight can be expected to be near the rubbery surface, and so the force moment may not be too high.

As will be readily apparent to one of skill in the art, there are various applications for this camera system.

One application involves breast imaging in which a patient is lying prone on a patient rest system with her breast pendant, and then wrapping the breast with the camera blanket, and using the magnet positioned below the breast to allow position measurement to occur, and then imaging the breast in as optimum a manner as possible. With this multihead design, it is necessary to be careful about the sternum area, because if both breasts are wrapped with a thick multihead, the two multiheads, one for the right breast and one for the left breast, might interfere with each other. For this reason, it may be necessary to image one breast and then the other, or it may only be necessary to image a suspect breast. The noise level between the right and left breast will also be different, because the left breast will have more heart noise than the right breast. For different women, the diameter of the wrapping of the breast will change. The average woman has an 11 cm breast diameter, and therefore the circumference of the average woman will be 11 pi which is approximately 34.54 cm. For a larger breasted woman with a 16 cm diameter, the circumference will be approximately 50.24 cm, and for a smaller woman the circumference is some amount smaller than 34 cm. A flexible mulithead that is hand positioned is able to accommodate these different breast sizes. A typical woman has a pendant breast length of about 11 cm, and so a typical multihead for this pendant breast application will allow a gamma camera area of 11 cm×50 cm.

Another application is related to breast lymph surgery, in which the sentinel lymph node of the patient needs to be identified prior to surgery. In this case, the multihead can be laid of the shoulder area of the supine patient after the technetium tracer is injected. If a magnet positioning system is used, the magnet may be below the patient's shoulder and underarm and breast tail area, and the multihead is overlaid on this area while spect imaging is done. A similar application design is possible for head and neck surgery, in which prior to a radical neck dissection the sentinel lymph node can be found by radioguidance methods, in which the multihead blanket is overlaid on the area of interest, and the magnet below the patient position allows magnetic position measurement of the gamma camera head positions. In these two lymph node applications, there is no need for a position movement system because the multihead blanket can be placed by hand in position over the area of interest, and then it can be removed after imaging has been completed to the surgeon's satisfaction.

Another usage example also relates to breast imaging. Currently in the marketplace, there are planar gamma cameras used for breast cancer screening, typically available from Dilon Diagnostic, Gamma-Medica and General Electric. These cameras have flat faces that cannot be flexed. In some cases, it would be useful to have a flat gamma camera for the start of the imaging session, and then, after a period of time, if a "hot" spot or lesion location is observed, the system control software could focus the gamma camera on the lesion of interest by flexing the gamma camera to more optimally point at the lesion. The purpose of this flexing is intended to increase the sensitivity, specificity, spatial accuracy, or perhaps could be used to reduce noise in the image. This flexible gamma camera approach may also lead to an ability to reduce the dosage of the imaging session.

As discussed herein, a flexible gamma camera system is described which will provide optimal imaging for various lesion requirements. The flexible gamma camera system can be used with an MRI system or by itself. It can use the MRI system to provide it with lesion information on which to curve the surface, or it can first image in the flat orientation and then curve the surface itself based on imaging results. This method can be used with various gamma energies, and therefore is suitable for various applications.

The curved surface will typically exist within a larger package, and the larger package will provide flexing hardware to allow the surface to flex.

The flex surface can be made of various materials and in various ways, including a firm rubber on which all of the gamma camera collimators and elements are glued, and including a metal or plastic hinge system that allow for the interconnection of all the collimators. For the case of the metal hinge system, as long as the metal hinges do not interfere with the front of the collimators, it is possible to use them. Also, metal hinges would not typically be used within a high magnetic field area such as near an MRI, unless the metal is of suitable metal that is not magnetic. It is also possible to embed a rubber grid between the collimator surfaces.

Also, the connection between Array 4 and electronics does not need to require the electronics card to be directly plugged into the Array 4. Instead, a ribbon cable or suitable connectorization and cabling can be used between the Array 4 and the electronics to allow the electronics to be positioned further away from the Array 4, which will allow easier packaging options and movement options in some applications.

Alternatively, instead of using a flex surface on which gamma camera elements are mounted, it is possible to use a flexible surface in which hinges or hinged surfaces between the gamma camera elements are used. In an application where the camera must stay on a plane and cannot be flexed as a whole, the individual elements, CSD (collimator, Scintillator and Detector) may be hinged or affixed onto a membrane in order to focus on the lesion of interest. The CSD will be moved either manually or with the use of a focusing driver/operation. The CSD will be connected to the electronics by a grouping of wires or cables in order to transfer the signals, shown below.

The flexing systems that have been discussed within this invention have illustrated 2-dimensional concave flexing.

The position measurement system can use the known orientation of the bottom of the gamma camera heads to improve the accuracy of the measurement. Unlike an object that can float freely in space, it is known a priori that the gamma camera elements are attached to the flexible substrate, and that the gamma camera elements remain side by side. For this reason, the convergence of the positioning algorithm may be that much quicker because of this known orientation between the gamma camera heads.

These gamma camera heads each have approximately 10 wires coming from the back, with the wires carrying 2 output signals, carrying in 4 voltage and ground signals, and carrying in a reset and clock line. In addition, monitoring and communications may require another 2 lines, and therefore in a typical case the readout boards have 10 wires connections. These 10 connections from each readout board are routed off of the gamma camera flexible substrate to a connection aggregator. The connection box allows a connection to occur to the external digital IFM system via an interface containing 4 power and ground lines, 2 lines for reset and clocking and 2×18=36 signal lines, for a total of 42 lines. The 4 power and ground lines are shared by all 18 gamma camera heads, the 2 reset and clock lines are also shared between all gamma camera heads, and the 2 signal lines from each gamma camera head must be routed back in their totality to the digital processing systems contained within the PC.

Figure 10:
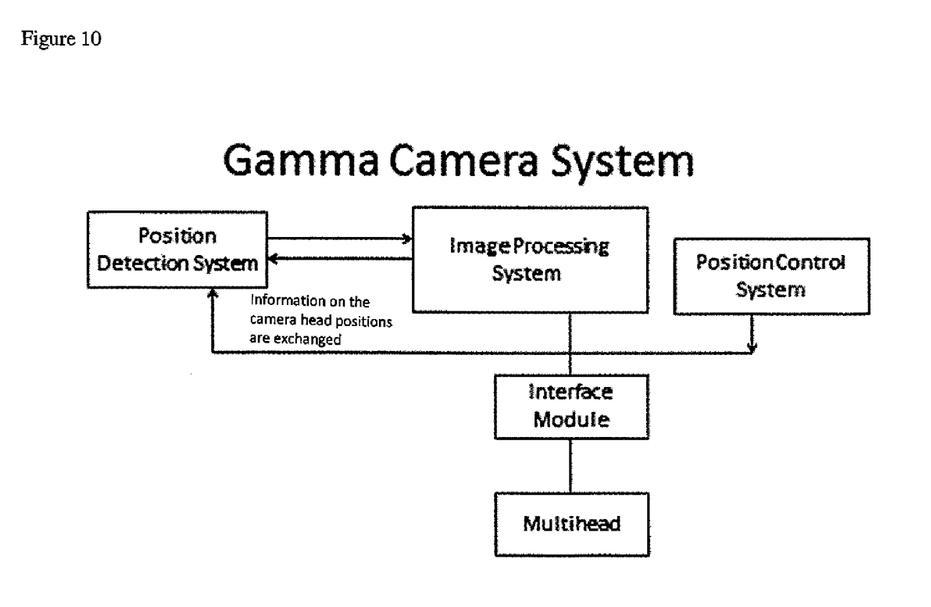
FIG. 10 shows the interconnection of the three basic subsystems in this design, which are the position detection system, the image processing system and the position control system. It indicates that the position movement system and the position measurement system are separate systems. In some designs, the position movement system is replaced by a hand positioning by the operator.

FIG. 10 shows the interconnection of the three basic subsystems in this design, which are the position detection system, the image processing system and the position control system. It indicates that the position movement system and the position measurement system are separate systems. In some designs, the position movement system consists of an operator positioning the unit by hand.

As part of the design of the multihead, MR, X-ray or Gamma fiducials may be used to allow image registration for multimodal image analysis and presentation. For example, in the case where MR and gamma images will both be used with a patient, it is possible that the multihead may be attached to a breast biopsy system, such as a square grid with fenestrations, and that the square grid will already have MR fiducials as part of its design. Once the multihead is attached on the square grid, the multihead package position would also be known via mechanical registration, and then the flexing portion of the multihead can be referenced to this known position.

While the preferred embodiments of the invention have been described above, it will be recognized and understood that various modifications may be made therein, and the appended claims are intended to cover all such modifications which may fall within the spirit and scope of the invention.

The invention claimed is:

1. A gamma camera imaging system comprising:
   a plurality of gamma camera heads, each respective one of said plurality of gamma camera heads comprising a collimator, a scintillator, a detector and a read-out system, each said respective one of said plurality of gamma camera heads being individually mounted to a flexible substrate;
   a flexible substrate capable of forming a concave inner surface and having an outer surface;
   an interface module; and
   an operating system,
   wherein each respective one of said plurality of gamma camera heads is mounted to the outer surface of the flexible substrate at a front face thereof.

2. The gamma camera imaging system according to claim 1 wherein the flexible substrate is arranged to form a concave surface for being fitted around a body portion.

3. The gamma camera imaging system according to claim 1 further comprising a movement system for moving said plurality of gamma cameras.

4. The gamma camera imaging system according to claim 1 further comprising a position identification system for determining the location of each respective one of the plurality of gamma camera heads.

5. A gamma camera system comprising:
   a flexible substrate capable of forming a concave inner surface and having an outer surface;
   a plurality of gamma camera heads, each respective one of said gamma camera heads comprising a collimator, scintillator, detector and read-out electronics system;
   a position identification system for determining the position of said each respective one of the plurality of gamma camera heads;
   a movement system for moving the flexible substrate and the respective ones of the plurality of gamma camera heads so as to optimize imaging parameters; and
   an operating system that controls movement and identification of positioning, and which provides gamma camera imaging software for planar or SPECT imaging,
   wherein each respective one of said plurality of gamma camera heads is mounted to the outer surface of the flexible substrate at a front face thereof.

* * * * *